United States Patent
Vasdev et al.

(10) Patent No.: US 9,546,167 B2
(45) Date of Patent: *Jan. 17, 2017

(54) RADIOSYNTHESIS OF TAU RADIOPHARMACEUTICALS

(71) Applicant: The General Hospital Corporation, Boston, MA (US)

(72) Inventors: Neil Vasdev, Cambridge, MA (US); Timothy M. Shoup, Franklin, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/087,681

(22) Filed: Mar. 31, 2016

(65) Prior Publication Data
US 2016/0214982 A1 Jul. 28, 2016

Related U.S. Application Data

(63) Continuation of application No. 14/892,949, filed as application No. PCT/US2014/040165 on May 30, 2014.

(60) Provisional application No. 61/829,679, filed on May 31, 2013.

(51) Int. Cl.
*C07D 471/04* (2006.01)
*C07B 59/00* (2006.01)

(52) U.S. Cl.
CPC ........... *C07D 471/04* (2013.01); *C07B 59/002* (2013.01)

(58) Field of Classification Search
CPC .............................. C07D 471/04; C07B 59/002

USPC .......................................................... 546/85
See application file for complete search history.

(56) References Cited

U.S. PATENT DOCUMENTS

| 6,685,912 | B2 | 2/2004 | Zamora et al. |
| 2012/0283490 | A1 | 11/2012 | Gangadharmath et al. |
| 2012/0302755 | A1 | 11/2012 | Szardenings et al. |

FOREIGN PATENT DOCUMENTS

WO 2009/102498 8/2009

OTHER PUBLICATIONS

International Search Report and Written Opinion mailed in international application No. PCT/US2014/040165, 14 pgs.
Shoup et al., "A Concise Radiosynthesis of the Tau Radiopharmaceutical, [$^{18}$F]T807," J Labelled Comp Radiopharm 56(14): 736-740 (2013).
Blom et al., "Preparative LC-MS Purification: Improved Compound-Specific Method Optimization," J. Comb. Chem., 2004, 6(6):874-883.
Chien, et al., "Early clinical PET imaging results with the novel PHF-tau radioligand [F-18]-T807," J. Alzheimers Dis., 2013, 34:457-68.
International Preliminary Report on Patentability in International Application No. PCT/US2014/040165, dated Dec. 1, 2015, 8 pages.
Xia, et al., "[(18)F]T807, a novel tau positron emission tomography imaging agent for Alzheimer's disease," Alzheimers Dement., Nov. 2013, 9:666-76.
Zhang, et al., "A highly selective and specific PET tracer for imaging of tau pathologies," J. Alzheimers Dis., 2012, 31.601-12.

*Primary Examiner* — Rita Desai
(74) *Attorney, Agent, or Firm* — Fish & Richardson P.C.

(57) ABSTRACT

This disclosure relates to a one-step method for preparing the tau radiopharmaceutical, [18F]T807, using an unprotected or protected precursor (e.g., tert-butyl 7-(6-nitropyridin-3-yl)-5H-pyrido[4,3-b]indole-5-carboxylate).

7 Claims, 2 Drawing Sheets

RADIOSYNTHESIS OF TAU RADIOPHARMACEUTICALS

CROSS-REFERENCE TO RELATED APPLICATIONS

This application is a continuation of U.S. patent application Ser. No. 14/892,949, filed on Nov. 20, 2015, which is a U.S. National Phase Application under 35 U.S.C. §371 of International Patent Application No. PCT/US2014/040165, filed on May 30, 2014, which claims priority to U.S. Provisional Application Ser. No. 61/829,679, filed on May 31, 2013, all of which are incorporated by reference in their entireties herein.

TECHNICAL FIELD

This disclosure relates to a one-step method for preparing the tau radiopharmaceutical, [$^{18}$F]T807, using an unprotected or protected precursor (e.g., tert-butyl 7-(6-nitropyridin-3-yl)-5H-pyrido[4,3-b]indole-5-carboxylate).

BACKGROUND

Development of positron emission tomography (PET) radiotracers that are specific for pathological tau accumulation in neurodegenerative diseases (tauopathies) represents one of the most active, yet most challenging, areas in neuroscience. Pioneering developments for tau imaging in human subjects have been achieved with [$^{18}$F]FDDNP, which is effective at imaging hyperphosphorylated tau fibrillar aggregates but does not distinguish between amyloid-β plaques and tau. Development of a selective and specific imaging agent is important for advancing our understanding of tauopathies, improving differential diagnostic accuracy, accelerating drug discovery and monitoring of therapeutics.

SUMMARY

An improved one-step synthesis method to prepare [$^{18}$F]T807 was achieved with a protected (e.g., t-BOC) precursor, offering increased solubility, a faster synthesis as well as simpler purification and automation. [$^{18}$F]T807 was validated for human use with a GE TRACERlab™ FX$_{FN}$ radiosynthesis module. The methodology demonstrated herein should facilitate multi-center trials and widespread use for tauopathy imaging with this radiopharmaceutical.

Provided herein is a process for preparing a compound of formula (II):

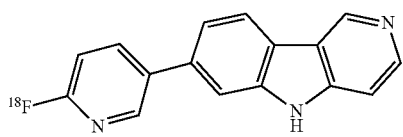 [SMILES: [18F]c1ccc(-c2ccc3c(c2)[nH]c2ccncc23)cn1]

the method comprising:
reacting a compound of formula (I):

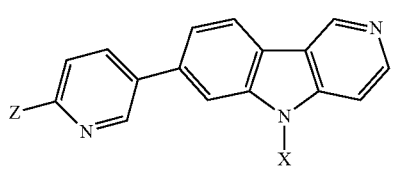

wherein:
X is H or a protecting group; and
Z is a leaving group,
with a radiofluorinating agent to prepare the compound of formula (II).

In some embodiments, X is a carbamate protecting group. For example, X can be t-butyl carbamate (Boc).

In some embodiments, Z is selected from the group consisting of: triflate, mesylate, nonaflate, hexaflate, tosylate, nosylate, brosylate, perfluoroalkyl sulfonate, tetraphenylborate, hexafluorophosphate, trifluoroacetate, tetrafluoroborate, perchlorate, perfluoroalkylcarboxylate, nitro, azide, chloride, bromide, or iodide. For example, Z can be nitro.

In some embodiments, the compound of formula (I) is:

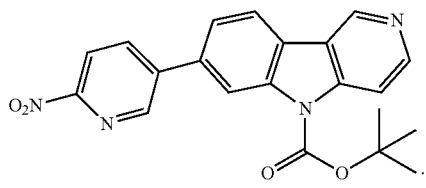 [SMILES: CC(C)(C)OC(=O)n1c2ccncc2c2ccc(-c3ccc([N+](=O)[O-])nc3)cc21]

In some embodiments, the radiofluorinating agent is potassium cryptand [$^{18}$F]fluoride (K[$^{18}$F]/K$_{222}$).

In some embodiments, the process is performed at a temperature ranging from about 60 to about 200° C. For example, the process can be performed at a temperature of about 130° C. In some embodiments, the heating occurs for a time period ranging from about 1 minutes to about 30 minutes. For example, the heating can occur for about 10 minutes.

In some embodiments, the process is performed in dimethylsulfoxide (DMSO).

The process can further include purifying the compound of formula (II) via HPLC. For example, the HPLC method can be an isocratic HPLC method.

In some embodiments, the compound of formula (II) is formulated with a carrier. For example, the carrier can be sodium chloride for injection, such as 0.9% sodium chloride for injection.

In some embodiments, the process can be performed in an automated radiosynthesis module.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Definitions

Figure 1:
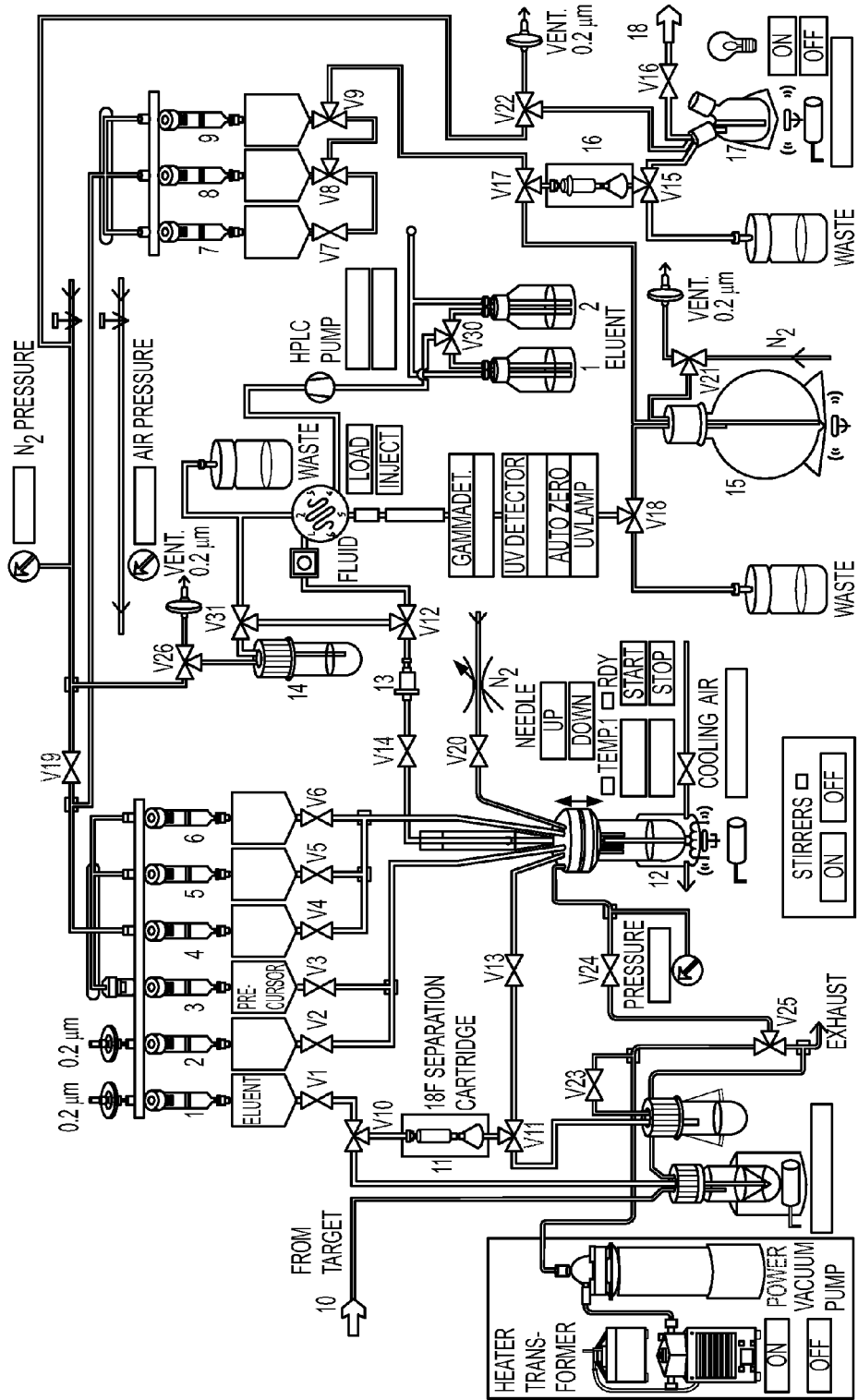
FIG. 1 is a schematic of the GE TRACERlab™ FX$_{FN}$ radiosynthesis module automated synthesis manifold for [$^{18}$F]T807.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

Unless defined otherwise, all technical and scientific terms used herein have the same meaning as is commonly understood by one of ordinary skill in the art to which this disclosure belongs. All patents, applications, published applications, and other publications cited herein are incorporated by reference in their entirety. In the event that there is a plurality of definitions for terms cited herein, those in this section prevail unless otherwise stated.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

In some embodiments, the compounds provided herein, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), which is incorporated herein by reference in its entirety) and normal phase silica chromatography.

Process for Preparing a Radiopharmaceutical

The radiopharmaceutical compounds, namely, [$^{18}$F]T807 (C. F. Xia, et al., *Alzheimers Dement.* 2013 in press. doi: 10.1016/j.jalz.2012.11.008; and D. T. Chien, et al., *J. Alzheimers Dis.* 2013, 34, 457-68) and [$^{18}$F]T808 (W. Zhang, et al., *J. Alzheimers Dis.* 2012, 31, 601-12) display excellent potency and selectivity in vitro for paired helical filaments of tau (PHF-tau) over Aβ-plaques, and both radiopharmaceuticals are currently in Phase 0 clinical studies for Alzheimer's disease. Whereas [$^{18}$F]T808 can be efficiently synthesized in one-step, the reported synthesis of [$^{18}$F]T807 involves a cumbersome, two-step reaction, that is automated using a modified Siemens Explora radiosynthesis module. After [$^{18}$F]fluorination of 7-(6-nitropyridin-3-yl)-5H-pyrido [4,3-b]indole (1a), a second step is carried out with iron powder/formic acid in a separate vial offline from the automated synthesis unit to reduce the nitro group on the remaining precursor to the respective amine (2-amino-pyridine), thereby facilitating HPLC separation. The cumbersome semi-automated reduction step is not readily adaptable to commercial radiosynthesis platforms and poses a challenge for multi-center trials and widespread use of this promising radiopharmaceutical.

Provided herein is an improved radiosynthesis of [$^{18}$F] T807 using a compound of formula (I) in a one-sten synthesis (Scheme 1).

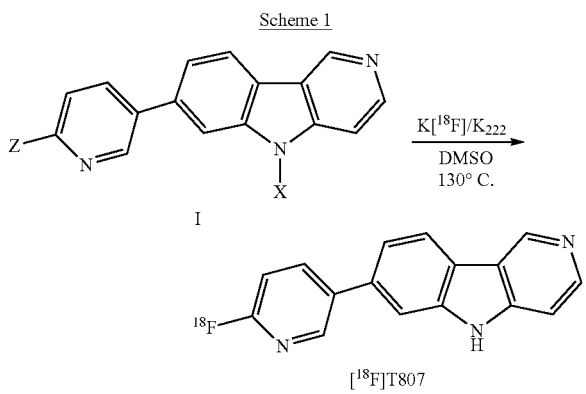

wherein:
X is H or a protecting group; and
Z is a leaving group.

As indicated, certain functional groups of the formula (I) structure (e.g., the nitrogen of the pyrrole ring) may be protected with an X protecting group. For this purpose, X may include any suitable amine protecting group (e.g. carbonate esters, carbamates, etc.).

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)] methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 2-phenylacetoxybenzyl carbamate (PhAcOZ), and m-chloro-p-acyloxybenzyl carbamate. In some embodiments, the carbamate protecting group is t-butyl carbamate (Boc).

A leaving group ("Z") as used herein can be any suitable leaving group. For example, Z can be a triflate (e.g., tetramethylammonium triflate), mesylate, nonaflate, hexaflate, tosylate, nosylate, brosylate, perfluoroalkyl sulfonate, tetraphenylborate, hexafluorophosphate, trifluoroacetate, tetrafluoroborate, perchlorate, perfluoroalkylcarboxylate, nitro, azide, chloride, bromide, or iodide. In some embodiments, Z is nitro.

A non-limiting example of a compound of formula (I) includes:

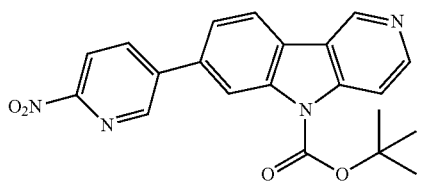 [SMILES: CC(C)(C)OC(=O)n1c2ccncc2c2ccc(-c3ccc([N+](=O)[O-])nc3)cc21]

tert-butyl 7-(6-nitropyridin-3-yl)-5H-pyrido[4,3-b]indole-5-carboxylate.

Compounds of formula (I) can be prepared using known organic synthesis methods. For example, the compounds can be prepared using methods as described in WO 2009/102498, which is incorporated by reference in its entirety.

The compound of formula (I) can be used to prepare the compound of formula (II):

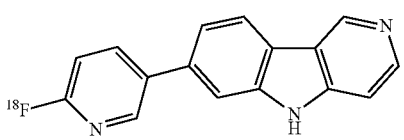 [SMILES: [18F]c1ccc(-c2ccc3c(c2)[nH]c2ccncc23)cn1]

([$^{18}$F]T807) in a one-step reaction. The process for preparing the compound of formula (II) includes reacting a compound of formula (I) as provided herein with a radiofluorinating agent to prepare the compound of formula (II).

A radiofluorinating agent can include any agent useful for introducing a radiolabeled fluorine atom ($^{18}$F). For example, the radiofluorinating agent can be selected from [$^{18}$F]TBAF, [$^{18}$F]Et4NF, [$^{18}$F]CsF, [$^{18}$F]AlF, other [$^{18}$F]Metal-fluorides, K[$^{18}$F], K$^{18}$F-crown-6, and potassium cryptand [$^{18}$F]fluoride (K[$^{18}$F]/K$_{222}$). In some embodiments, the radiofluorinating agent is potassium cryptand [$^{18}$F]fluoride (K[$^{18}$F]/K$_{222}$).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

In some embodiments, the reactions described herein can be performed in dimethyl sulfoxide (DMSO), dimethyl formamide, acetonitrile, and mixtures thereof. In some embodiments the reactions can be performed in DMSO.

The process for preparing a compound of formula (II) can be performed as any suitable temperature. For example, the process is performed at a temperature ranging from about 60 to about 200° C. (e.g., about 80 to about 160° C., and about 100 to about 150° C.). In some embodiments, the process is performed at a temperature greater than about 60° C. In some embodiments, the process is performed at a temperature of about 130° C. In some embodiments, the temperature may be reduced to room temperature under pressure and flow chemistry conditions (e.g., microfluidics) or through the use of microwave heating.

The heating can occur for a time period necessary to prepare a suitable amount of a compound of formula (II). For example, the heating can occur for a time period ranging from about 1 minute to about 30 minutes (e.g., about 1 minute to about 15 minutes; about 1 minute to about 10 minutes, about 1 minute to about 5 minutes, about 1 minute to about 2 minutes, about 5 minutes to about 30 minutes, about 10 minutes to about 30 minutes, about 20 minutes to about 30 minutes, about 5 minutes to about 15 minutes, about 2 minutes to about 18 minutes, and about 7 minutes to about 13 minutes). In some embodiments, the heating can occur for about 10 minutes.

Following the above described reaction, the compound of formula (II) can be purified prior to formulation. In some embodiments, the compound of formula (II) is purified via HPLC. For example, the compound of formula (II) can be purified using an isocratic HPLC method.

Following the reaction described above, the compound of formula (II) can be formulated with a pharmaceutically acceptable carrier. For example, the pharmaceutically acceptable carrier can be sodium chloride for injection. In some embodiments, the carrier is 0.9% sodium chloride for injection.

As described herein, the reaction to prepare a compound of formula (II) from a compound of formula (I) occurs in a single-step. Accordingly, the process may be performed manually or effectively in an automated radiosynthesis module. Any suitable radiosynthesis module may be used. For example, a GE TRACERlab™ FX$_{FN}$ radiosynthesis module.

A non-limiting example of the process provided herein is provided in Scheme 2.

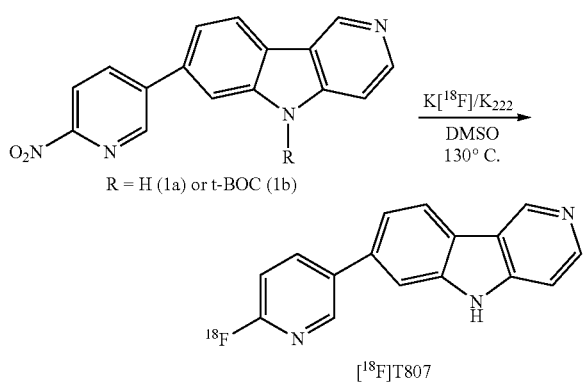

In some embodiments, a compound (1a or 1b) and optimized isocratic HPLC separation conditions provide a facile one-step synthesis of [$^{18}$F]T807. In some such embodiments, compound 1b is concurrently deprotected during the nucleophilic fluorinating reaction with potassium cryptand [$^{18}$F] fluoride (K[$^{18}$F]/K$_{222}$) in DMSO at 130° C. over 10 minutes to provide the compound of formula (II).

EXAMPLES

The invention is further described in the following examples, which do not limit the scope of the invention described in the claims.

General Methods—Chemicals and Reagents

Compounds 1a, 1b, and authentic standard, 7-(6-fluoro-pyridin-3-yl)-5H-pyrido[4,3-b]indole (T807), were custom synthesized to GMP standards. All other chemicals and reagents were obtained from commercial vendors and were used as received without further purification.

Example 1

Automated Synthesis of [$^{18}$F]T807

A GE PETtrace 16/8.5 MeV cyclotron was used for [$^{18}$F]fluoride radionuclide production. A GE high yield niobium target containing >97% enriched O-18 water (Isotec, Taiyo Nippon Sanso or Rotem) was bombarded with protons at integrated currents up to 65 µA to produce [$^{18}$F]fluoride. Following completion of bombardment, the [$^{18}$F]fluoride was transferred to the TRACERlab™ FX$_{FN}$ radiosynthesis module via helium gas overpressure.

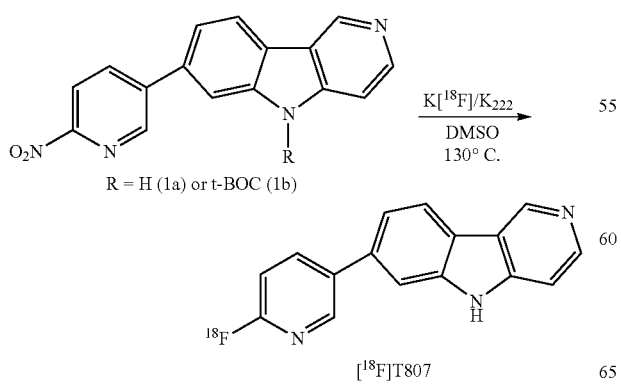

Figure 2:
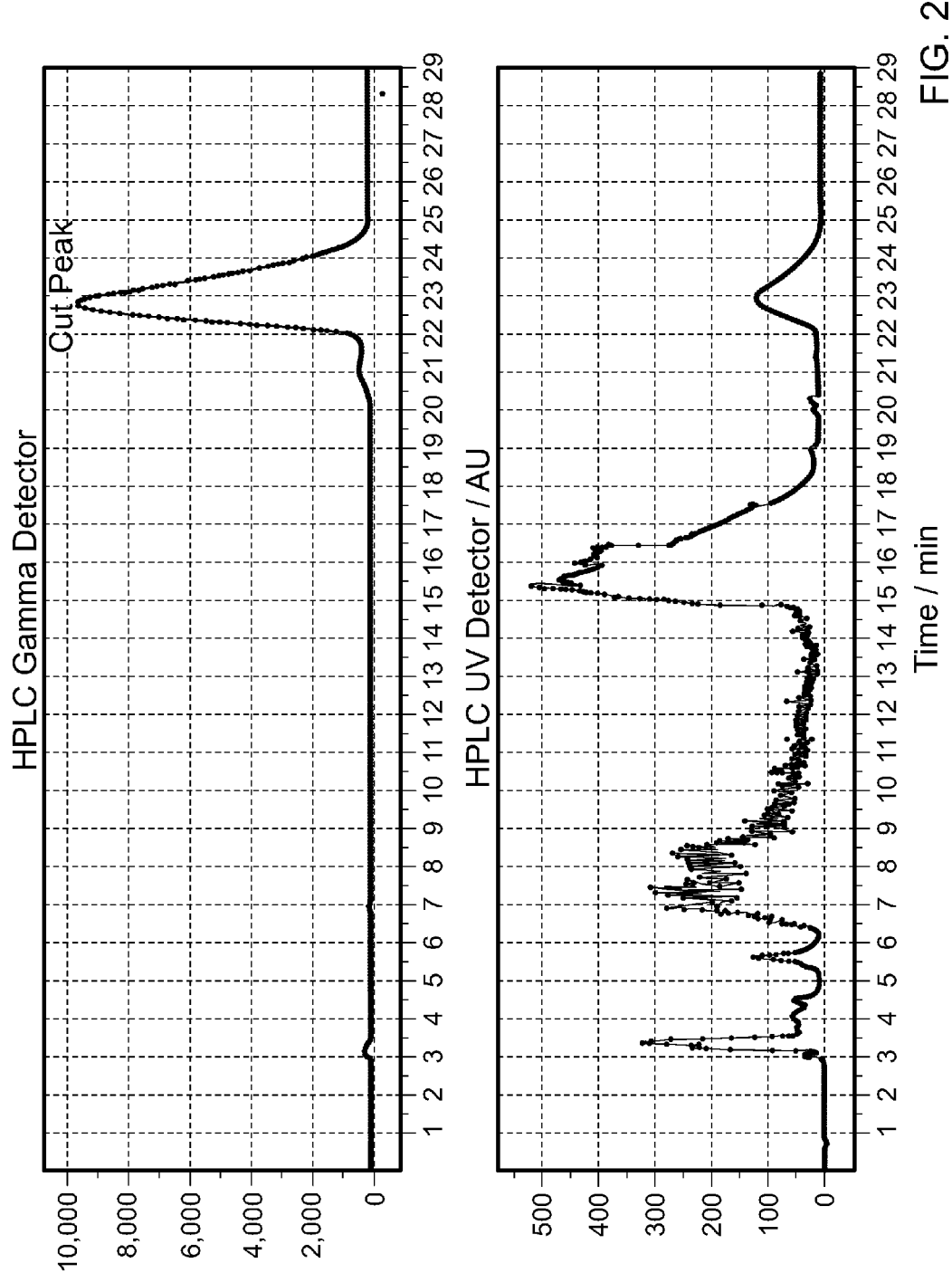
FIG. 2 shows a semi-Preparative HPLC trace (18/82 ethanol/H$_2$O (v/v)+0.1% conc. HCl (pH 2), LUNA 10μ C18(2), (250×10.00 mm, 4.2 mL/min) of a typical radiosynthesis of [$^{18}$F]T807, synthesized using a GE TRACERlab™ FX$_{FN}$ radiosynthesis module: Gamma (t$_R$=13.8 min; top), and UV (λ=254 nm; bottom). Units on Y-axis are arbitrary.

A schematic diagram of the GE medical systems commercial TRACERlab™ FX$_{FN}$ radiosynthesis module used for the synthesis of [$^{18}$F]T807 is shown in FIG. 1. Automated synthesis involves: (1) azeotropic drying of [$^{18}$F] fluoride, (2) [$^{18}$F]fluorination of 1 (Scheme 1), (3) in-line solvent exchange and (4) HPLC purification, followed by solid-phase formulation of the final product. The synthesis module was operated in the following sequences, with numerical references to FIG. 1:

1. [$^{18}$F]Fluoride was produced by the $^{18}$O(p,n)$^{18}$F nuclear reaction, using a GE cyclotron and delivered to the radiosynthesis module, via line 10. The [$^{18}$F]fluoride was quantitatively trapped on a QMA carbonate ion exchange solid phase extraction (SPE) light cartridge 11 (Waters; activated with 6 mL of trace grade H$_2$O).
2. Automated synthesis began with the elution of resin-bound [$^{18}$F]fluoride (37±0.37 GBq; 1.0±0.1 Ci) using 1 mL of a solution (15 mg K$_{222}$, 1.5 mg K$_2$CO$_3$, 0.6 mL trace grade H$_2$O, 0.6 mL acetonitrile), pre-loaded into vessel 1, and delivered to the reaction vial 12.
3. The reaction mixture in vial 12 was azeotropically dried by addition of 1 mL anhydrous CH$_3$CN, pre-loaded into vessel 4, at 85° C., under N$_2$ flow and vacuum, over 8 min, then at 110° C., under N$_2$ flow and vacuum for 4 min.
4. After heating to 130° C., the precursor (1a or 1b), 1 mg in 1.5 mL DMSO; pre-loaded into vessel 3 was added to vial 12. The reactor was sealed via valve V24 and the reaction occurred for 10 min.
5. Subsequently, the reaction mixture was cooled to 50° C., vented via valves V24 and V25, and diluted with 10 mL of H$_2$O, pre-loaded into vessel 5.
6. The contents of vial 12 were delivered onto a Oasis® HLB Light SPE cartridge (Waters; pre-activated with 5 mL EtOH followed by 10 mL H$_2$O), 13 and washed with 5 mL of water from vessel 6 to remove DMSO, unreacted $^{18}$F-fluoride and other impurities. The crude reaction mixture was eluted from the cartridge with 1 mL of ethanol from vessel 2 into vessel 14 containing 1 mL of water. The contents of vessel 14 were transferred to the HPLC loop via nitrogen overpressure, via a fluid detector, injected onto a semi-preparative column (X-Select HSS T3, 250×10.00 mm, 5µ), and eluted with 18% EtOH/H$_2$O by volume (pH 2, adjusted with HCl) at a flow rate of 5 mL/min. The eluent was monitored by a UV (λ=254 nm) and radiochemical detector connected in series.
7. A typical semi-preparative HPLC chromatogram is shown in FIG. 2. The fraction containing the major radiochemical product (t$_R$=21.5 min) was collected, via valve 18, into a large dilution vessel 15 which was pre-loaded with 2 mL 8.4% sodium bicarbonate for injection, USP (Hospira) and 23 mL of sterile water for injection, USP.
8. The product was loaded onto an Oasis® HLB Light SPE cartridge, (Waters; pre-activated with 5 mL EtOH followed by 10 mL H$_2$O), 16.
9. The SPE cartridge was then washed to a waste container with 10 mL H$_2$O, pre-loaded into vessel 7 to remove traces of salts, CH$_3$CN, and [$^{18}$F]fluoride.
10. The SPE cartridge was eluted with 1 mL USP EtOH, pre-loaded into vessel 8, into collection vial 17, followed by 10 mL 0.9% sodium chloride for injection, USP, pre-loaded into vessel 9.
11. The solution was transferred, via line 18, and passed through a 0.22 µm PES vented sterilizing filter (B. Braun) connected to a 16 gauge hypodermic needle into a sterile 30 mL dose vial (Hospira) fitted with a sterile filtered venting needle (International Medical Industries)

Analyses of radioactive mixtures were performed by HPLC with an in-line UV (λ=254 nm) detector in series with a CsI pin diode radioactivity detector. To determine the identity of [$^{18}$F]T807, aliquots of the formulated product were injected onto an analytical HPLC system using a X-Select HSS T3, 150×4.6 mm, 3.5 µm and eluted with 20% EtOH/H$_2$O (pH 2 adjusted with HCl) with a flow rate of 1.2 mL/min, monitored at λ=254 nm. The major radiochemical product was identified as [$^{18}$F]T807 ($t_R$=8.8 min).

The uncorrected radiochemical yield (RCY) of [$^{18}$F]T807 was 14±3% (n=3) and the total synthesis time was 60 minutes, including formulation. The product was prepared consistently with >95% radiochemical purity and the specific activity at the end of synthesis was 216±60 GBq/µmol (5837±1621 mCi/µmol). In the previous radiosynthesis method used for human validation of [$^{18}$F]T807 (see D. T. Chien, et al., *J. Alzheimers Dis.* 2013, 34, 457-68), precursor, 1a was used and resulted in ~17% uncorrected RCY at the end of synthesis (EOS; 93 minutes) with specific activities >1 mCi/µmol at the time of injection. Under the reaction conditions described herein, it was found that radiolabelling was more efficient when the precursor was in the t-BOC protected form (ib), because its solubility was increased in the reaction solvent (DMSO), compared with 1a which was only sparingly soluble in most organic solvents. Therefore, the precursor could be added remotely to the reaction vial with minimal volume and eliminated the possibility of the precursor precipitating out of solution before use. Moreover, the fluorination condition simultaneously removed the t-BOC protecting group so there was no need for an additional deprotection step. Secondly, without being bound by any theory, it is thought that the protecting group may also be responsible for the higher radiochemical yields by inhibiting side reactions with the —NH of the indole moiety.

Following $^{18}$F-fluorination in the original published procedures using 1a, an additional step was carried out where the reaction mixture was heated at 100° C. for 15 min in a separate vial containing iron powder/formic acid to reduce the —NO$_2$ group on the unused precursor to the respective amine (aniline) in order to facilitate HPLC separation of [$^{18}$F]T807 from the precursor. It was found that this step can be eliminated by using a suitable isocratic HPLC separation conditions for purification of [$^{18}$F]T807. Hence, the overall synthesis was simplified to a one-step reaction followed by isocratic HPLC separation. The unprotected precursor (1a) was evaluated (n=1) using the optimized reaction identified above on the FX$_{FN}$ radiosynthesis module. The uncorrected radiochemical yield for this reaction was much lower (2.4%) and specific activity at end of synthesis was 133 GBq/µmol (3615 mCi/µmol). The majority of the activity (55%) was isolated in the SPE waste (FIG. 1; 13), and was identified as unreacted [$^{18}$F]fluoride by radio-TLC.

Example 2

Validation for Human Use

Three consecutive productions of [$^{18}$F]T807 were carried out to validate this radiopharmaceutical for human use. HPLC analysis of formulated [$^{18}$F]T807 revealed high radiochemical (>95%) and chemical purities. Due to the increased lipophilicity of 1b, an additional HPLC analysis was performed using an X-Select HSS T3 column (4.6×150 mm, 3.5 µm) and eluted with 50% CH$_3$OH/H$_2$O (pH 2 adjusted with HCl) with a flow rate of 1.2 mL/min, monitored at λ=254 nm. Radio-TLC was performed to verify the radiochemical purity of [$^{18}$F]T807 using silica gel plates and 80:20 (v/v) CH$_2$Cl$_2$:CH$_3$OH mobile phase. Radio-TLC confirmed high radiochemical purity (>97%). The integrity of the final filter was demonstrated by a bubble point filter test (>50 psi). Formulated [$^{18}$F]T807 maintained stability, as measured by HPLC and radio-TLC, as well as clarity and a pH of 5.5 over a period of 6 hours. The half-life was verified to be 109.7 minutes, as determined by a dose calibrator, and no long lived isotopes were observed (5 days), as determined by analysis on a HPGE detector after $^{18}$F-decay. Formulated [$^{18}$F]T807 was free of pyrogens (Charles River Endosafe® PTS), sterile, and passed the Kryptofix® spot test (<50 µg/mL). Volatile organic compound analysis, via GC-FID, showed residual acetone, CH$_3$CN and DMSO below the lower limit of detection, exceeding ICH requirements. Using this new methodology, [$^{18}$F]T807 was successfully validated for human PET studies, meeting all FDA and USP requirements for a PET radiopharmaceutical.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula (I):

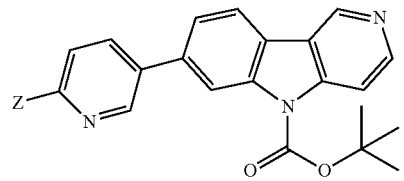

wherein Z is a leaving group.

2. The compound of claim 1, wherein the leaving group comprises: triflate, mesylate, nonaflate, hexaflate, tosylate, nosylate, brosylate, perfluoroalkyl sulfonate, tetraphenylborate, hexafluorophosphate, trifluoroacetate, tetrafluoroborate, perchlorate, perfluoroalkylcarboxylate, nitro, azide, chloride, bromide, or iodide.

3. The compound of claim 1, wherein the leaving group is tetramethylammonium triflate.

4. The compound of claim 1, wherein the compound of formula (I) is:

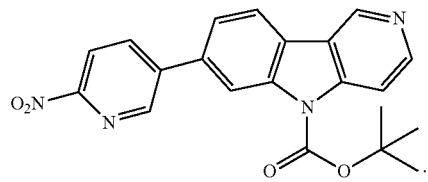 [SMILES: CC(C)(C)OC(=O)n1c2ccncc2c2ccc(-c3ccc([N+](=O)[O-])nc3)cc21]

5. A compound of formula (I):
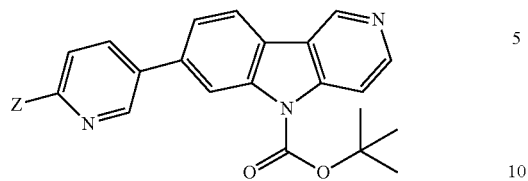
wherein Z is a leaving group comprising tetramethylammonium.
6. The compound of claim 5, wherein the leaving group further comprises: triflate, mesylate, nonaflate, hexaflate, tosylate, nosylate, brosylate, and perfluoroalkyl sulfonate.
7. The compound of claim 5, wherein the leaving group further comprises triflate.
* * * * *